United States Patent
Matsuo et al.

(10) Patent No.: US 10,401,285 B2
(45) Date of Patent: Sep. 3, 2019

(54) APPARATUS FOR MEASURING SURFACE PROPERTIES OF POLISHING PAD

(71) Applicants: EBARA CORPORATION, Tokyo (JP); Kyushu Institute of Technology, Fukuoka (JP)

(72) Inventors: Hisanori Matsuo, Tokyo (JP); Keiichi Kimura, Fukuoka (JP); Keisuke Suzuki, Fukuoka (JP); Panart Khajornrungruang, Fukuoka (JP); Takashi Kushida, Fukuoka (JP)

(73) Assignees: EBARA CORPORATION, Tokyo (JP); Kyushu Institute of Technology, Fukuoka (JP)

( * ) Notice: Subject to any disclaimer, the term of this patent is extended or adjusted under 35 U.S.C. 154(b) by 267 days.

(21) Appl. No.: 14/024,405

(22) Filed: Sep. 11, 2013

(65) Prior Publication Data
US 2014/0262027 A1    Sep. 18, 2014

(30) Foreign Application Priority Data
Mar. 12, 2013  (JP) .................................. 2013-49685

(51) Int. Cl.
*G01B 11/30*   (2006.01)
*G01N 21/47*   (2006.01)
*B24B 37/005*  (2012.01)

(52) U.S. Cl.
CPC ....... *G01N 21/4738* (2013.01); *B24B 37/005* (2013.01); *G01B 11/303* (2013.01)

(58) Field of Classification Search
USPC .................................................... 156/345.13
See application file for complete search history.

(56) References Cited

U.S. PATENT DOCUMENTS 3,866,038 A * 2/1975 Korth .................. G01B 11/303
                                                250/236
5,413,941 A * 5/1995 Koos ..................... B24B 37/013
                                                 438/16
(Continued)

FOREIGN PATENT DOCUMENTS

JP    09-119822 A    5/1997
JP    09-285955 A    11/1997
(Continued)

OTHER PUBLICATIONS

Kushida et al.; "Study on evaluation method for surface topography of CMP polishing pad based on optical Fourier transform"; The Japan Society for Precision Engineering Autumn Meeting Academic Conference Lecture Paper; 2011; distributed Sep. 20, 2011; p. 159-160.

(Continued)

*Primary Examiner* — Gordon Baldwin
*Assistant Examiner* — Mirza Israr Javed
(74) *Attorney, Agent, or Firm* — Baker & Hostetler LLP

(57) ABSTRACT

The present invention relates to an apparatus for measuring surface properties of a polishing pad which measures surface properties such as surface topography or surface condition of a polishing pad used for polishing a substrate such as a semiconductor wafer. The apparatus for measuring surface properties of a polishing pad includes a laser beam source configured to emit a laser beam, and a photodetector configured to detect scattered light that is reflected and scattered by the polishing pad, an optical Fourier transform being performed on the detected scattered light to produce an intensity distribution corresponding to a spatial wavelength spectrum based on surface topography of the polishing pad. The laser beam is applied to the polishing pad at such an (Continued)

incident angle that the laser beam does not reach a bottom portion of a pore formed in the surface of the polishing pad.

12 Claims, 13 Drawing Sheets

(56) References Cited

U.S. PATENT DOCUMENTS

| | | | | |
|---|---|---|---|---|
| 5,433,650 | A * | 7/1995 | Winebarger | B24B 37/013 257/E21.244 |
| 5,483,568 | A * | 1/1996 | Yano | H01L 21/3212 257/E21.304 |
| 5,517,312 | A * | 5/1996 | Finarov | G01B 11/065 356/630 |
| 5,708,506 | A * | 1/1998 | Birang | B24B 49/12 356/600 |
| 5,733,171 | A * | 3/1998 | Allen | B24B 37/0053 451/41 |
| 5,823,853 | A * | 10/1998 | Bartels | B24B 37/0053 451/5 |
| 5,934,974 | A * | 8/1999 | Tzeng | B24B 37/013 257/E21.23 |
| 6,040,244 | A * | 3/2000 | Arai | B24B 37/005 438/691 |
| 6,045,434 | A * | 4/2000 | Fisher, Jr. | B24B 49/183 451/10 |
| 6,435,948 | B1 * | 8/2002 | Molnar | B24B 1/005 451/262 |
| 6,517,413 | B1 * | 2/2003 | Hu | B24B 37/013 451/285 |
| 6,670,200 | B2 * | 12/2003 | Ushio | B24B 37/013 257/E21.528 |
| 6,684,704 | B1 * | 2/2004 | Obeng | B24B 37/005 451/21 |
| 7,070,479 | B2 * | 7/2006 | Faustmann | B24B 49/02 451/21 |
| 7,198,546 | B2 * | 4/2007 | Berman | B24B 37/04 451/28 |
| 2001/0015801 | A1 * | 8/2001 | Hirose | B24B 37/20 356/237.2 |
| 2002/0137434 | A1 * | 9/2002 | Choi | B24B 37/20 451/28 |
| 2003/0060127 | A1 * | 3/2003 | Kaushal | B24B 37/20 451/8 |
| 2003/0123067 | A1 * | 7/2003 | Chuang | B24B 37/042 356/504 |
| 2006/0164104 | A1 * | 7/2006 | Tada | G01B 15/02 324/646 |
| 2006/0181700 | A1 * | 8/2006 | Andrews | G01N 21/21 356/237.2 |
| 2007/0015442 | A1 * | 1/2007 | Shin | B24B 37/042 451/8 |
| 2012/0064800 | A1 * | 3/2012 | Watanabe | B24B 37/005 451/5 |

FOREIGN PATENT DOCUMENTS

| | | |
|---|---|---|
| JP | 2003-151934 A | 5/2003 |
| JP | 2008-002891 A | 1/2008 |
| JP | 2010-023210 A | 2/2010 |
| JP | 2012-137484 A | 7/2012 |
| KR | 10-2002-0040487 | 5/2002 |
| KR | 10-2010-0028665 | 3/2010 |

OTHER PUBLICATIONS

Kushida et al.; "Study on evaluation method for surface topography of CMP polishing pad based on optical Fourier transform"; $2^{nd}$ Report—Development of Measuring System; The Japan Society for Precision Engineering Spring Meeting Academic Conference Lecture Paper; 2012; distributed Mar. 14, 2012; p. 823-824.

Kushida et al.; "Study on evaluation method for surface topography of CMP polishing pad based on optical Fourier transform"; The Japan Society for Precision Engineering Spring Meeting Academic Conference Lecture Paper; 2011; distributed Sep. 20, 2011; p. 159-160.

* cited by examiner

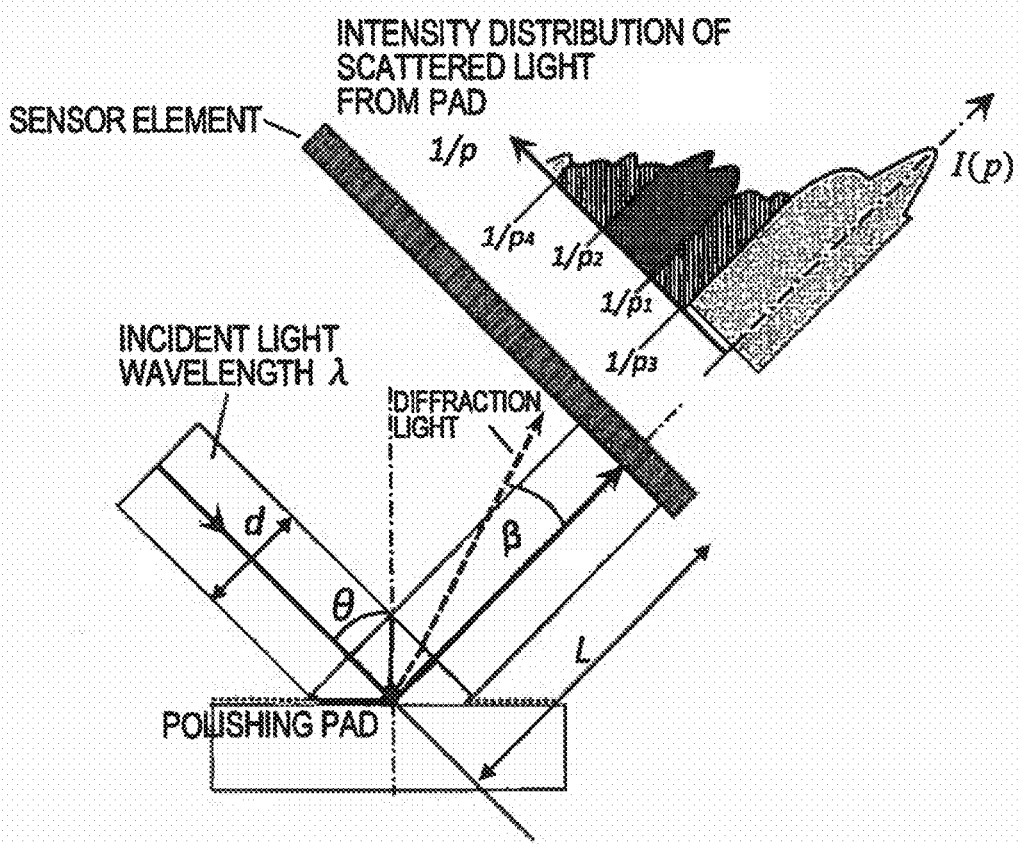

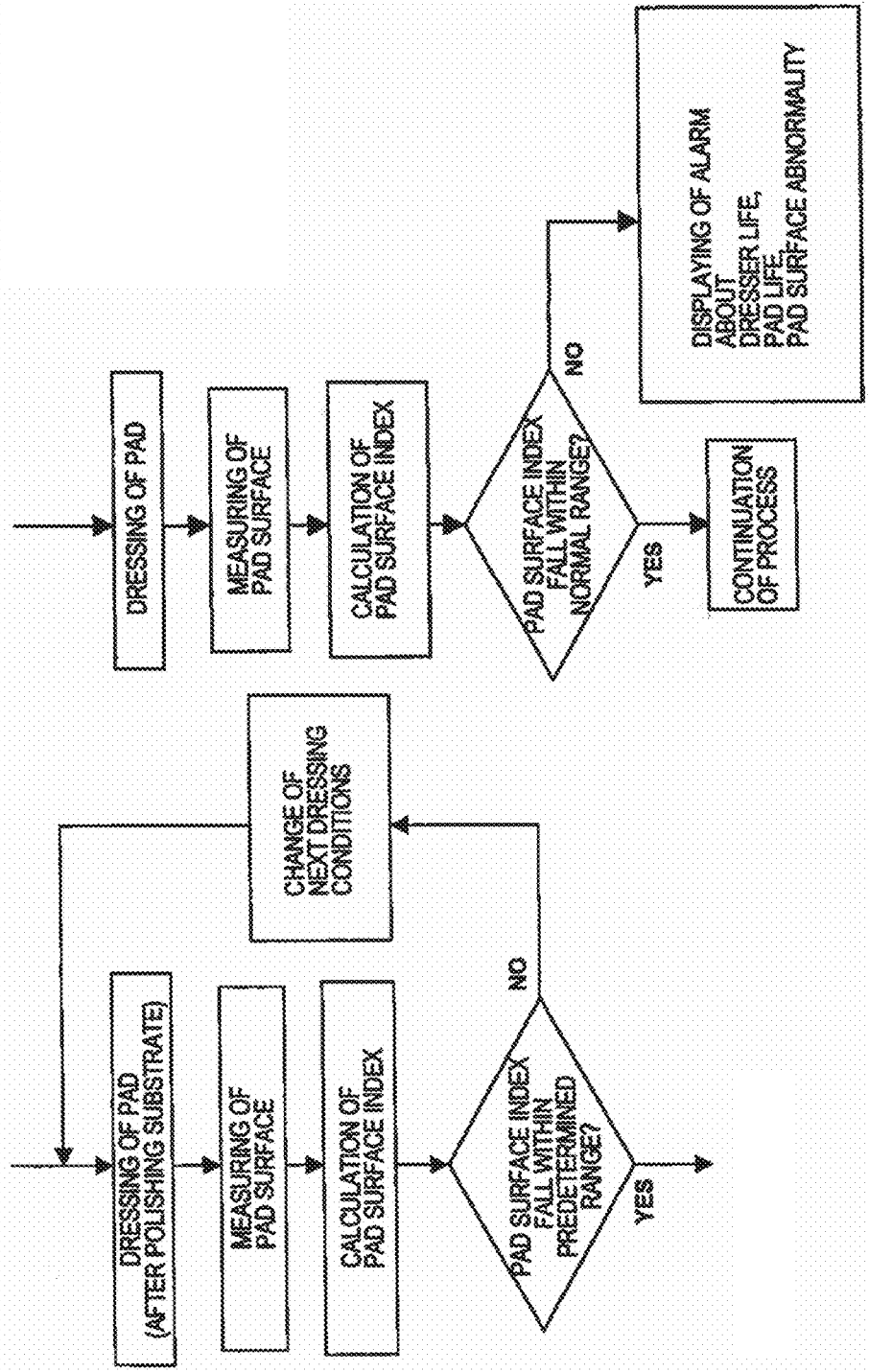

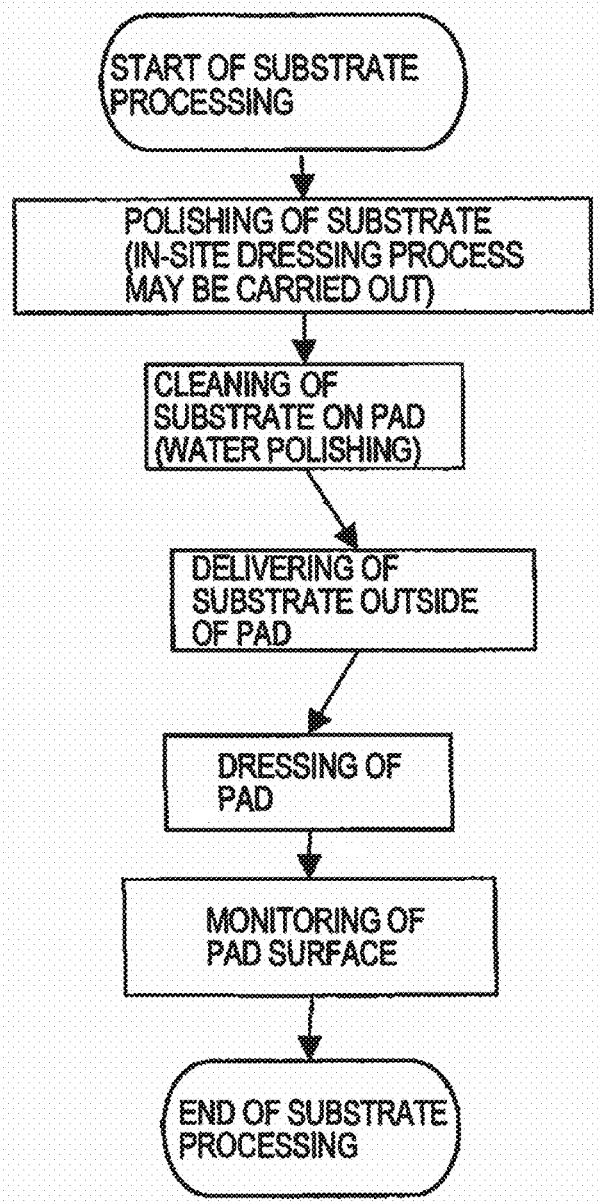

APPARATUS FOR MEASURING SURFACE PROPERTIES OF POLISHING PAD

CROSS REFERENCE TO RELATED APPLICATIONS

This application claims priority to Japanese Patent Application No. 2013-49685 filed Mar. 12, 2011, the entire contents of which are hereby incorporated by reference.

BACKGROUND OF THE INVENTION

Field of the Invention

The present invention relates to an apparatus for measuring surface properties of a polishing pad which measures surface properties such as surface topography or surface condition of a polishing pad used for polishing a substrate such as a semiconductor wafer.

Description of the Related Art

In recent years, high integration and high density in semiconductor device demands smaller and smaller wiring patterns or interconnections and also more and more interconnection layers. Multilayer interconnections in smaller circuits result in greater steps which reflect surface irregularities on lower interconnection layers. An increase in the number of interconnection layers makes film coating performance (step coverage) poor over stepped configurations of thin films. Therefore, better multilayer interconnections need to have the improved step coverage and proper surface planarization. Further, since the depth of focus of a photolithographic optical system is smaller with miniaturization of a photolithographic process, a surface of the semiconductor device needs to be planarized such that irregular steps on the surface of the semiconductor device will fall within the depth of focus.

Thus, in a manufacturing process of a semiconductor device, it increasingly becomes important to planarize a surface of the semiconductor device. One of the most important planarizing technologies is chemical mechanical polishing (CMP). In the chemical mechanical polishing, using a polishing apparatus, while a polishing liquid containing abrasive particles such as silica ($SiO_2$) or ceria ($CeO_2$) therein is supplied onto a polishing pad, a substrate such as a semiconductor wafer is brought into sliding contact with the polishing pad, so that the substrate is polished.

The polishing apparatus for performing the above CMP process includes a polishing table having a polishing pad, and a substrate holding device, which is referred to as a carrier or a top ring, for holding a substrate such as a semiconductor wafer. By using such a polishing apparatus, the substrate is held and pressed against the polishing pad under a predetermined pressure by the substrate holding device, thereby polishing an insulating film or a metal film on the substrate.

After one or more substrates have been polished, abrasive particles in a polishing liquid or ground-off particles of the substrate are attached to the surface of the polishing pad, and surface configuration or surface condition of the polishing pad is changed, resulting in deterioration in polishing performance. Therefore, as the substrates are repeatedly polished by the same polishing pad, a polishing rate is lowered and nonuniform polishing action is caused. Thus, dressing (conditioning) of the polishing pad is performed using a dresser to regenerate the surface configuration or surface condition of the polishing pad which has deteriorated.

In the CMP (Chemical Mechanical Polishing) process, the surface topography and condition of the polishing pad have a significant influence on the polishing performance, and thus it has been proposed to measure the surface topography and condition of the polishing pad with various measuring processes and to reflect the measured data in dressing conditions and polishing conditions.

The following documents 1 and 2 suggest that when a laser beam is applied to a surface of a polishing pad, the surface topography of the polishing pad can be measured by an optical FFT analysis of diffused reflection light from the polishing pad.

1. Takashi Kushida, Keiichi Patent Khajomrungruang, Keisuke Suzuki "Study on evaluation method for surface topography of CMP polishing pad based on optical Fourier transform ($2^{nd}$ report)—Development of measuring system—", 2012 The Japan Society for Precision Engineering Spring Meeting Academic Conference Lecture Papers, distributed Mar. 14, 2012, p. 823-824.
2. Takashi Kushida, Keiichi Kimura, Panart Khajnomungruang Keisuke Suzuki "Study on evaluation method for surface topography of CMP polishing pad based on optical Fourier transform", 2011 The Japan Society for Precision Engineering Autumn Meeting Academic Conference Lecture Papers, distributed Sep. 20, 2011, p. 159-160.

When a laser beam is applied to a surface of a polishing pad, and the surface properties such as surface topography or surface condition of the polishing pad is measured using diffused reflection fight from the polishing pad, there are effects of various disturbances and the like, and thus it is important to detect the diffused reflection light appropriately.

SUMMARY OF THE INVENTION

The present invention has been made in view of the above circumstances. It is therefore an object of the present invention to provide an apparatus for measuring surface properties of a polishing pad and a polishing apparatus having such measuring apparatus which can measure surface properties of the polishing pad accurately by suppressing effects of various disturbances and the like.

In order to achieve the above object, according to a first aspect of the present invention, there is provided an apparatus for measuring surface properties of a polishing pad which is held in sliding contact with a substrate to polish a surface of the substrate, comprising a laser beam source configured to emit a laser beam, and a photodetector configured to detect scattered light that is reflected and scattered by the polishing pad, an optical Fourier transform being performed on the detected scattered light to produce an intensity distribution corresponding to a spatial wavelength spectrum based on surface topography of the polishing pad, wherein the laser beam is applied to the polishing pad at such an incident angle that the laser beam does not reach a bottom portion of a pore formed in the surface of the polishing pad.

According to a second aspect of the present invention, there is provided an apparatus for measuring surface properties of a polishing pad which is held in sliding contact with a substrate to polish a surface of the substrate, comprising a laser beam source configured to emit a laser beam, and a photodetector configured to detect scattered light that is reflected and scattered by the polishing pad, an optical Fourier transform being performed on the detected scattered light to produce an intensity distribution corresponding to a spatial wavelength spectrum based on surface topography of the polishing pad, wherein the laser beam is applied to the polishing pad at such an incident angle that the reflectance of the light from the surface of the polishing pad is 50% or greater.

According to a third aspect of the present invention, there is provided an apparatus for measuring surface properties of a polishing pad which is held in sliding contact with a substrate to polish a surface of the substrate, comprising a laser beam source configured to emit a laser beam, and a photodetector configured to detect scattered light that is reflected and scattered by the polishing pad, an optical Fourier transform being performed on the detected scattered light to produce an intensity distribution corresponding to a spatial wavelength spectrum based on surface topography of the polishing pad, wherein the laser beam is S-polarized and is then applied to the surface of the polishing pad.

According to a preferred aspect of the present invention, the laser beam is applied to the polishing pad at such an illuminating angle that the reflectance of the light from the surface of the polishing pad is 50% or greater.

According to the present invention, the laser beam emitted from the laser beam source is applied to the polishing pad at such an incident angle that the laser beam does not reach a bottom portion of a pore formed in the surface of the polishing pad. Thus, effects due to the presence of the pore can be suppressed, and the surface properties of the polishing pad can be measured accurately by suppressing effects of disturbances and the like.

Similarly, according to the present invention, the laser beam emitted from the laser beam source is applied to the polishing pad at such an incident angle that the reflectance of the light from the surface of the polishing pad is 50% or greater, or the laser beam emitted from the laser beam source is S-polarized and is then applied to the surface of the polishing pad. Thus, effects caused by the laser beam which has entered the polishing pad can be suppressed, and the surface properties of the polishing pad can be measured accurately by suppressing effects of disturbances and the like.

According to another aspect of the present invention, there is provided a polishing apparatus comprising a carrier configured to hold a substrate as an object to be polished and to press the substrate against the polishing pad, a polishing table configured to hold the polishing pad and rotate the polishing pad, a dresser configured to dress the polishing pad, and an apparatus for measuring surface properties of a polishing pad according to any one of claims 1 to 4.

The present invention may have the following aspects using a numerical value representing the surface properties of the polishing pad which are obtained by the apparatus for measuring surface properties of a polishing pad according to any one of claims 1 to 4:

1) A method of dressing a polishing pad under dressing conditions that are set based on the numerical value representing the surface properties of the polishing pad which are obtained by the apparatus for measuring surface properties of a polishing pad according to any one of claims 1 to 4.

2) A method of detecting a life of a dresser based on the numerical value representing the surface properties of the polishing pad which are obtained by the apparatus for measuring surface properties of a polishing pad according to any one of claims 1 to 4.

3) A method of detecting a life of a polishing pad based on the numerical value representing the surface properties of the polishing pad which are obtained by the apparatus for measuring surface properties of a polishing pad according to any one of claims 1 to 4.

4) A method of detecting an abnormality of surface properties of a polishing pad based on the numerical value representing the surface properties of the polishing pad which are obtained by the apparatus for measuring surface properties of a polishing pad according to any one of claims 1 to 4.

According to the present invention, the surface properties of the polishing pad can be measured accurately by suppressing effects of various disturbances and the like. Further, the following stable operation of CMP can be performed using the measured values.

(1) The cost of consumable materials can be reduced because the polishing pad and the dresser can be used up until the end of their lives.

(2) Since an unsteady state of the surface properties of the polishing pad due to a dressing abnormality can promptly be detected and an alarm can be activated, any semiconductor device fabrication failure owing to a CMP performance fault can be minimized.

(3) The surface properties of the polishing pad can be maintained in a state required to maintain the CMP performance by changing dressing conditions depending on a change in the surface properties of the polishing pad.

BRIEF DESCRIPTION OF THE DRAWINGS

FIG. 7 is a schematic diagram showing an intensity distribution of scattered light that is reflected and scattered by the surface of the polishing pad when the polishing pad is irradiated with a laser beam;

FIGS. 12A and 12B are flowcharts of sequences for changing dressing conditions using numerical values obtained by the process shown in FIG. 3 and sequences for displaying an alarm; and FIG. 13 is a diagram showing an example of sequences for polishing a substrate, dressing a polishing pad and monitoring a surface of the polishing pad, using the polishing apparatus configured as shown in FIGS. 1 and 2.

DETAILED DESCRIPTION OF THE PREFERRED EMBODIMENTS

Figure 1:
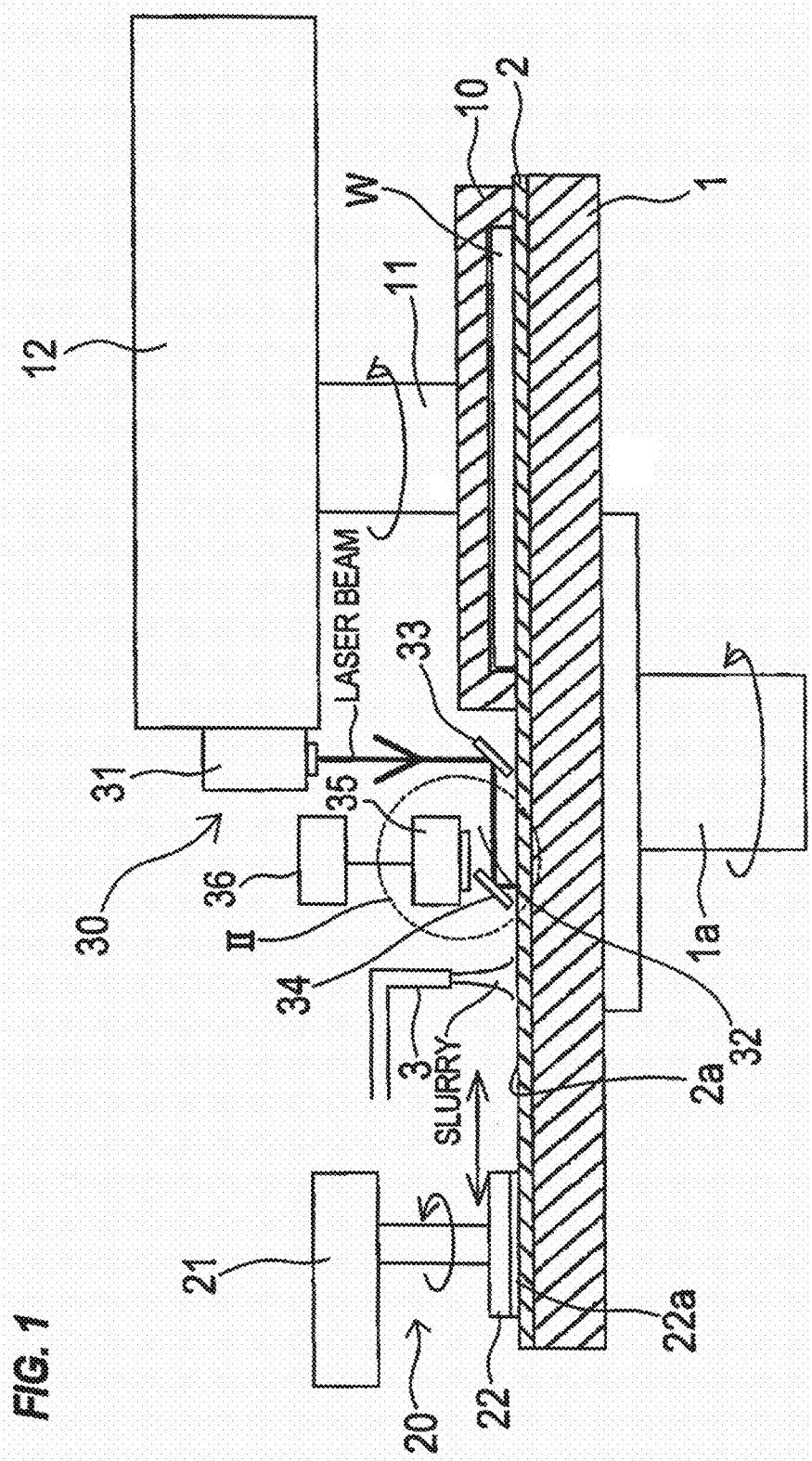
FIG. 1 is a schematic view showing an entire structure of a polishing apparatus having a surface property measuring device of a polishing pad according to the present invention.

An apparatus for measuring surface properties of a polishing pad according to an embodiment of the present invention will be described below with reference to FIGS. 1 through 13. Like or corresponding parts are denoted by like or corresponding reference numerals in FIGS. 1 through 13 and will not be described in duplication.

FIG. 1 is a schematic view showing an entire structure of a polishing apparatus having a surface property measuring device of a polishing pad according to the present invention. As shown in FIG. 1, the polishing apparatus comprises a polishing table 1, and a carrier 10 for holding a substrate W such as a semiconductor wafer as an object to be polished and pressing the substrate against a polishing pad on the polishing table. The polishing table 1 is coupled via a table shaft 1a to a polishing table rotating motor (not shown) disposed below the polishing table 1. Thus, the polishing table 1 is rotatable about the table shaft 1a. A polishing pad 2 is attached to an upper surface of the polishing table 1. An upper surface of the polishing pad 2 constitutes a polishing surface 2a for polishing the substrate W. The polishing pad 2 comprising SUBA 800, IC-1000, IC-1000/SUBA400 (two-layer cloth) or the like manufactured by the Dow Chemical Company is used. The SUBA 800 is non-woven fabrics bonded by urethane resin. The IC-1000 comprises a pad composed of hard polyurethane foam and having a large number of fine holes (pores) formed in its surface, and is also called a perforated pad. A polishing liquid supply nozzle 3 is provided above the polishing table 1 to supply a polishing liquid (slurry) onto the polishing pad 2 on the polishing table 1.

The carrier 10 is connected to a shaft 11, and the shaft 11 is vertically movable with respect to a carrier arm 12. When the shaft 11 moves vertically, the carrier 10 is lifted and lowered as a whole for positioning with respect to the carrier arm 12. The shaft 11 is configured to be rotated by driving a motor (not shown). The carrier 10 is rotated about an axis of the shaft 11.

As shown in FIG. 1, the carrier 10 is configured to hold the substrate W such as a semiconductor wafer on its lower surface. The carrier arm 12 is configured to be pivotable, and thus the carrier 10, which holds the substrate W on its lower surface, is movable from a position at which the carrier 10 receives the substrate to a position above the polishing table 1 by pivotable movement of the Gather arm 12. Then, the carrier 10 holds the substrate W on its lower surface and presses the substrate W against the surface (polishing surface) of the polishing pad 2. At this time, while the polishing table 1 and the carrier 10 are respectively rotated, a polishing liquid (slurry) is supplied onto the polishing pad 2 from the polishing liquid supply nozzle 3 provided above the polishing table 1. The polishing liquid containing silica ($SiO_2$) or ceria ($CeO_2$) as abrasive particles is used. In this manner, while the polishing liquid is supplied onto the polishing pad 2, the subsite W is pressed against the polishing pad 2 and is moved relative to the polishing pad 2 to polish an insulating film, a metal film or the like on the substrate. Examples of the insulating film include $SiO_2$, and examples of the metal film include a Cu film, a W film, a Ta film and all film.

As shown in FIG. 1, the polishing apparatus has a dressing apparatus 20 for dressing the polishing pad 2. The dressing apparatus 20 comprises a dresser arm 21, and a dresser 22 which is rotatably attached to a forward end of the dresser turn 21. The lower part of the dresser 22 comprises a dressing member 22a, and the dressing member 22a has a circular dressing surface. Hard particles are fixed to the dressing surface by electrodeposition or the like. Examples of the hard particles include diamond particles, ceramic particles and the like. A motor (not shown) is provided in the dresser arm 21, and the dresser 22 is rotated by the motor. The dresser arm 21 is coupled to a lifting and lowering mechanism (not shown), and the dresser arm 21 is lowered by the lifting and lowering mechanism to allow the dressing member 22a to be pressed against the polishing surface 2a of the polishing pad 2. Equipments including the polishing table 1, the carrier 10, the dressing apparatus 20 and the like are connected to a controller (not shown), and the rotational speed of the polishing table 1, the rotational speed and the polishing pressure of the carrier 10, the load and the oscillating speed of the dresser 22 in the dressing apparatus 20, and the like are controlled by the controller.

As shown in FIG. 1, the polishing apparatus has a polishing pad surface property measuring device 30 for measuring surface properties such as surface topography or surface condition of the polishing pad 2. The polishing pad surface property measuring device 30 includes a laser beam source 31 for emitting a laser beam, a light guide space 32 for guiding the laser beam so that the laser beam travels substantially parallel to the surface of the polishing pad 2, a mirror 34 for changing a traveling direction of the laser beam which travels substantially parallel to the surface of the polishing pad 2 to a substantially vertical direction with respect to the surface of the polishing pad 2, and a photodetector 35 for detecting scattered light that is reflected and scattered by the surface of the polishing pad 2. The laser beam source 31 emits a laser beam having a wavelength of 408 era. According to the embodiment shown in FIG. 1, the laser beam source 31 is fixed to the carrier arm 12, and the laser beam emitted from the laser beam source 31 is led to the light guide space 32 by a mirror 33. Specifically, the laser beam that is emitted substantially perpendicularly from the laser beam source 31 has its light path changed by the mirror 33, and is led to the light guide space 32. In the light guide space 32, the laser beam travels substantially parallel to the surface of the polishing pad 2, and then the laser beam has its light path changed by the mirror 34, and is applied substantially perpendicularly to the polishing pad 2. The photodetector 35 for detecting scattered light that is reflected and scattered by the surface of the polishing pad 2, which comprises an area sensor, is disposed above the surface of the polishing pad 2 so that the photodetector 35 can detect scattered light down to a low wavelength range that greatly affects the CMP performance. The photodetector 35 may comprise a CMOS sensor, a photodiode array, or a photomultiplier array.

The polishing pad surface property measuring device 30 includes a processing device 36 having a processing function to convert an intensity distribution of scattered light detected by the photodetector 35 into numerical values correlated to the CMP performance according to a particular processing method. The processing device 36 is connected to the photodetector 35. The processing device 36 has a processing function to convert an intensity distribution (spectrum) of scattered light into numerical values correlated to the CMP performance according to a particular processing method. The processing device 36 also has a display function to display the intensity distribution of scattered light and the numerical values correlated to the CMP performance. The processing device 36 may be incorporated in a CMP controller. Signals from the processing device 36 are inputted into the CMP controller.

Figure 2:
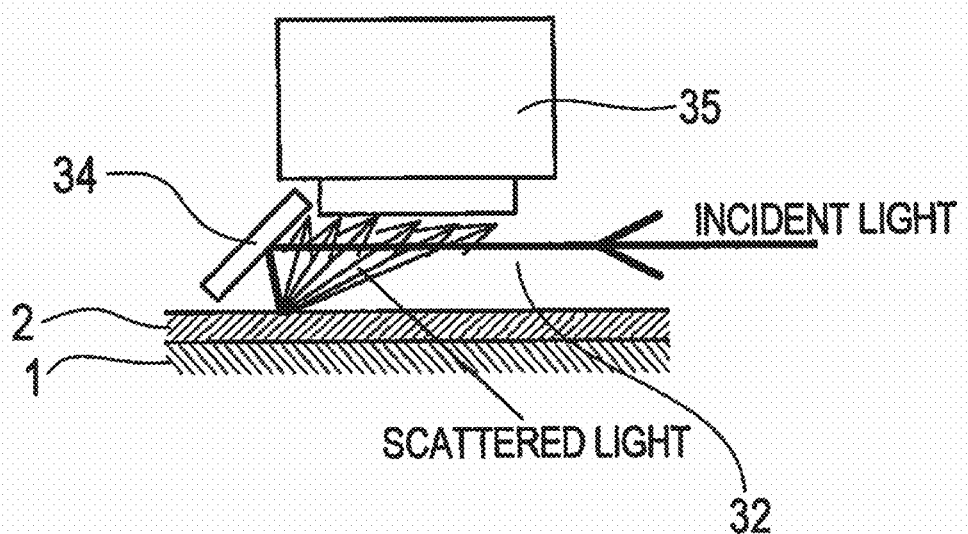
FIG. 2 is an enlarged view of an encircled area II in FIG. 1.

FIG. 2 is au enlarged view of an encircled area II in FIG. 1. An incident light, which is the laser beam emitted from the laser beam source 31, has its light path changed by the mirror 33 (see FIG. 1), and is led to the light guide space 32. As shown in FIG. 2, the laser beam travels substantially parallel to the surface of the polishing pad 2 in the light guide space 32, and then the laser beam has its light path changed by the mirror 34, and is applied substantially perpendicularly to the polishing pad 2. Scattered light that is reflected and scattered by the surface of the polishing pad 2 is detected by the photodetector 35.

Figure 3:
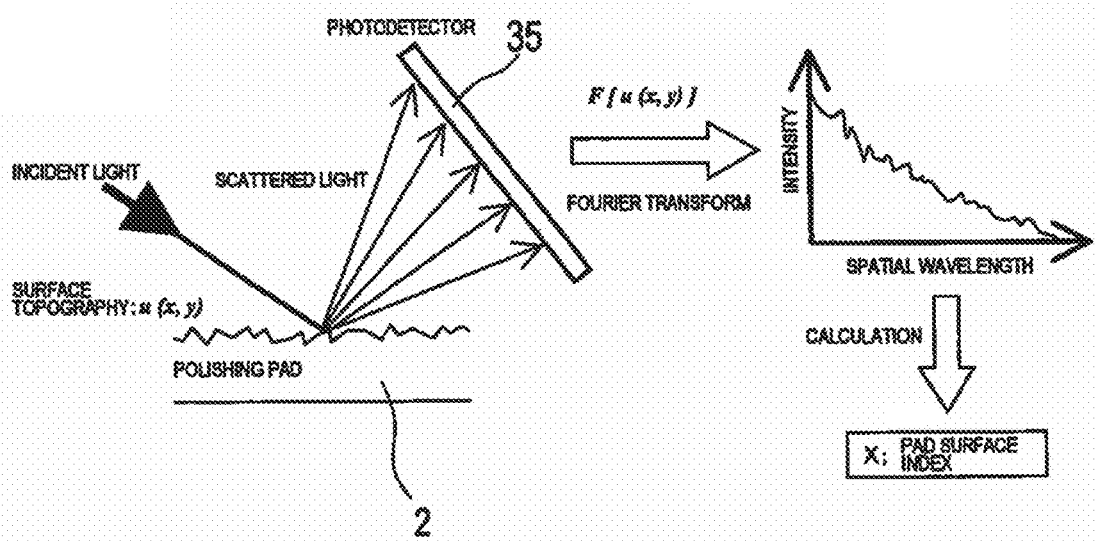
FIG. 3 is a schematic diagram showing a process of capturing an image (detecting light) and arithmetically processing the image into numerical values, which is carried out by the surface property measuring device shown in FIGS. 1 and 2.

FIG. 3 is a schematic diagram showing a process of capturing an image (detecting light) and arithmetically processing the image into numerical values, which is carried out by the polishing pad surface property measuring device 30 shown in FIGS. 1 and 2. In FIG. 3, the photodetector 35 is schematically shown in terms of its shape and location, and the laser beam source 31, the mirror 34, and the processing device 36 are omitted from illustration.

As shown in FIG. 3, the surface property measuring device 30 performs the following steps:

(1) The surface property measuring device 30 applies a laser beam to the polishing pad 2 which has surface topography u(x, y).

(2) The photodetector 35 detects scattered light that is reflected and scattered by the surface of the polishing pad, and obtains an intensity distribution of scattered light. The intensity distribution of scattered light represents a distribution obtained by Fourier transform of the surface topography of the polishing pad with its spatial wavelengths.

(3) The processing device 36 determines a pad surface index according to predetermined processing sequences.

The predetermined processing sequences are as follows:
An integrated value of the intensity of the scattered light in a certain spatial wavelength range.
The ratio of an integrated value in a second spatial wavelength range to an integrated value in a first spatial wavelength range.

Specific processes and device configurations for performing the above steps (1) to (3) will be described below.

Figure 4:
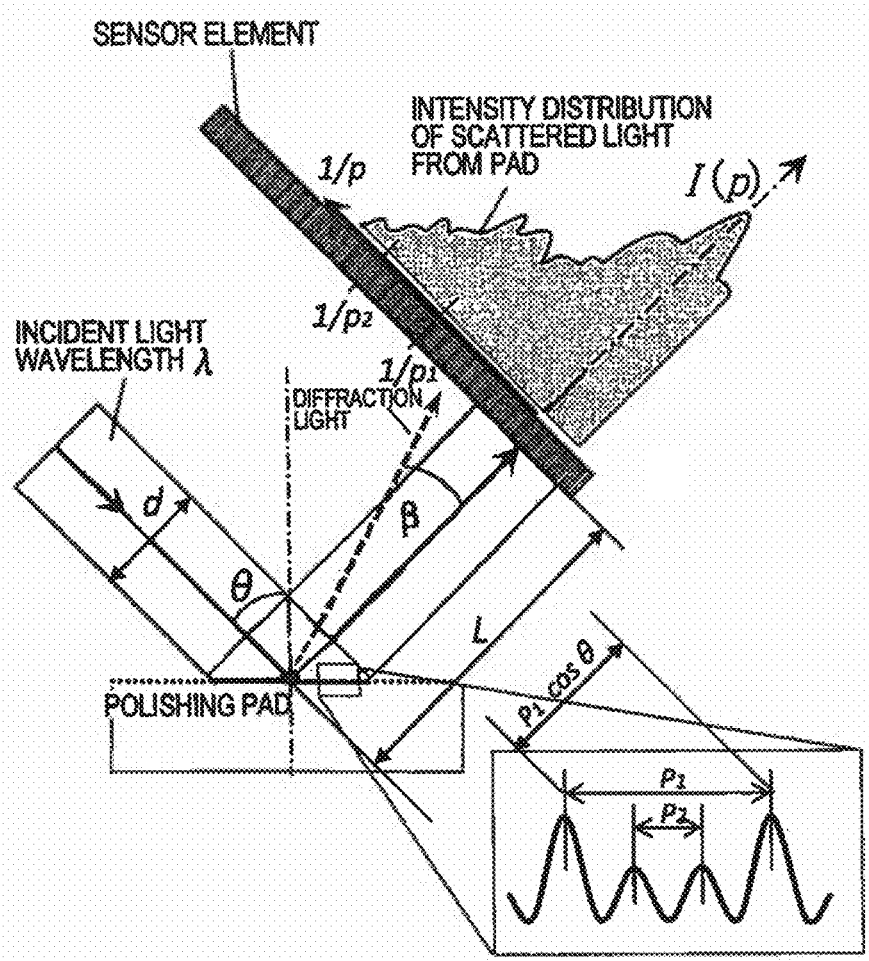
FIG. 4 is a schematic diagram showing an intensity distribution of scattered light caused by pad surface topography when the polishing pad is irradiated with a laser beam.

1) An Intensity Distribution of Scattered Light from the Polishing Pad:

FIG. 4 is a schematic diagram showing an intensity distribution of scattered light caused by pad surface topography when the polishing pad is irradiated with a laser beam.

It is assumed that, as shown in FIG. 4, an intensity distribution I(p) of scattered light caused by pad surface topography when the polishing pad is irradiated with a laser beam (wavelength λ) is observed by a photodetector. Positions 1/p on the photodetector indicate a spectrum of spatial wavelengths p that represent surface irregularities of the polishing pad. Specifically, the light intensity distribution indicates a spectrum of spatial Fourier transform of the surface topography of the polishing pad. For example, in the case of a relatively long spatial wavelength $p_1$, its spectrum appears at the position $1/p_1$ (spatial frequency range) of the photodetector. The same holds true for a relatively short spatial wavelength $p_2$.

In FIG. 4, the symbols are defined as follows:
θ: Incident angle
d: Laser beam diameter
ß: Diffraction angle (angle through which diffracted light deviates from specularly reflected light)
L: Distance between the photodetector and the polishing pad
p: Spatial wavelength of the surface topography of the polishing pad The equation for determining the diffraction angle (ß) is represented by the equation (1) which is determined by the applied wavelength λ, the established incident angle θ, and the spatial wavelength p of surface irregularities. The condition for the equation (1) needs to be far-field diffraction. According to far-field diffraction, it is necessary that the observing photodetector be spaced by a sufficient distance L from the polishing pad, as indicated by the equation (2). It can be seen from the equation (1) that if the spatial wavelength p becomes smaller than the laser wavelength λ as shown in the equation (3), then the diffraction angle becomes greater than 90°, and the laser beam is not reflected, but is absorbed, by the surface of the polishing pad.

$$p \cos \theta \sin ß + p \sin \theta (1 - \cos ß) = \lambda \quad (1)$$

$$\text{The condition for far-field diffraction: } L \gg (p \cos \theta)^2 / 2\lambda \quad (2)$$

$$\text{The condition for the spatial wavelength and the laser beam wavelength: } p/\lambda > 1 \quad (3)$$

Figure 5:
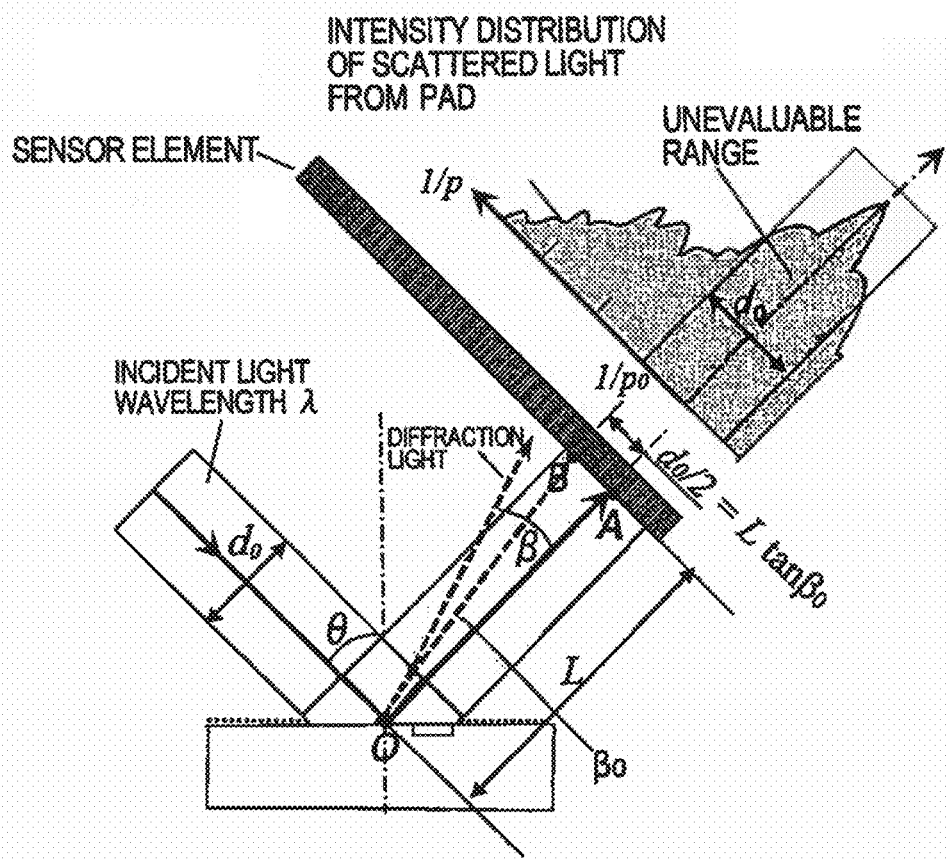
FIG. 5 is a schematic diagram showing the relationship between the distance between the photodetector and the polishing pad and the laser spot diameter.

2) Study of the Distance Between the Photodetector and the Polishing Pad and the Laser Spot Diameter:

FIG. 5 is a schematic diagram showing the relationship between the distance between the photodetector and the polishing pad and the laser spot diameter. The symbols in FIG. 5 are defined in the same manner as in FIG. 4.

If the incident angle is expressed as θ=45° and L is greater than 100 times $p^2/4\lambda$ in the equation (2), then the distance L between the photodetector and the polishing pad needs to satisfy the condition indicated by the equation (2.1).

$$L > 100(p^2/4\lambda) \quad (2.1)$$

Within the region of a laser beam diameter $d_0$, the diffraction light (range of $ß < ß_0$) overlaps the specularly reflected light (width $d_0$) and hence cannot be evaluated. Therefore, a diffraction angle ß (spatial frequency 1/p) that is greater than a diffraction angle $ß_0$ (spatial frequency $1/p_0$ of the corresponding pad surface irregularities on the photodetector) becomes an evaluable range ($ß > ß_0$ or $1/p_0$).

At the boundary of the specularly reflected light, $AB/OA = \tan ß_0 = d_0/2 L$.

Because the distance is expressed as $L \gg d_0$, if $(d_0^2 + 4 L^2)^{1/2}$ is nearly equal 2 L, i.e. $(d_0^2 + 4 L^2)^{1/2} \approx 2 L$, then it is possible to approximate $\sin ß_0 \approx d_0/2 L$ and $\cos ß_0 = 2 L(d_0^2 + 4 L^2)^{1/2} \approx 2 L/(4 L^2)^{1/2} = 1$.

From the equation (1), the range of spatial wavelengths 1/p that can be evaluated is $1/p_0 = (\cos \theta \sin ß_0 + \sin \theta (1 - \cos ß_0))/\lambda < 1/p$, and thus the following condition is obtained:

$$p \cos \theta \times (d_0/2L) < \lambda \quad (4)$$

i) Selection of the distance L between the photodetector and the polishing pad:

For example, in the case where the polishing pad is IC1000, the pore diameter of the polishing pad is in the range of 40 to 60 µm, and thus spatial wavelengths are evaluated as $p < p_0 = 30$ µm.

Further, if the laser wavelength is set to $\lambda = 0.532$ µm, the distance is expressed as $L > 100 \times (30$ µm$)^2/4(0.532$ µm$) \approx 43$ mm.

Thus, for example, the distance L between the photodetector and the polishing pad may be selected as $L > 50$ mm.

ii) Selection of the laser spot diameter $d_0$:

Under the boundary conditions of the range that cannot be evaluated, the laser spot diameter $d_0$ is given as $d_0 < 4$ (50 mm)(0.532 µm)/$2^{1/2}$(30 µm) = 2.5 mm.

For example, the laser spot diameter may be selected as $d < 2$ mm.

Figure 6:
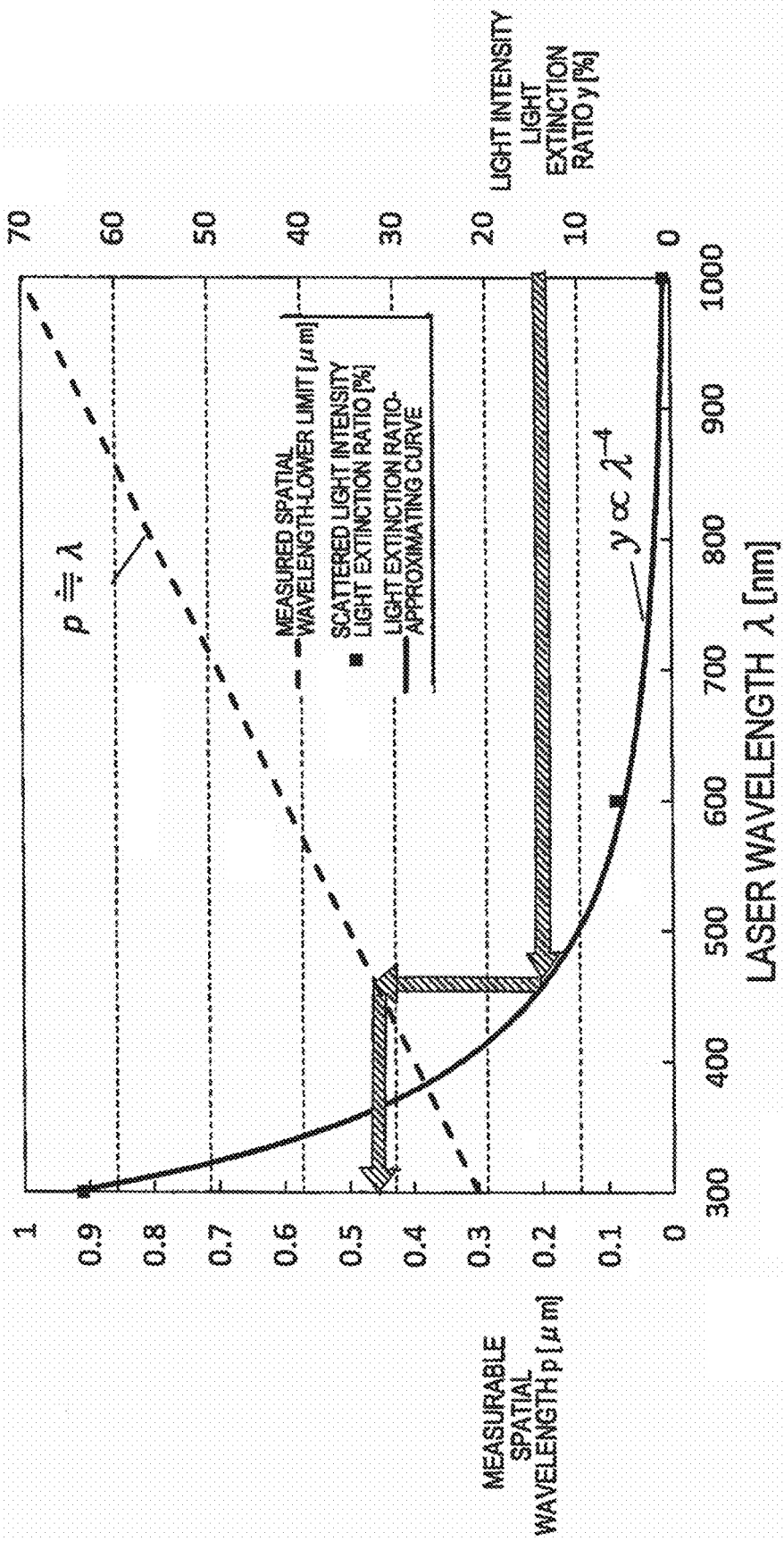
FIG. 6 is a graph showing the relationship between laser wavelengths ($\lambda$ [nm]) and measurable spatial wavelengths (p [$\mu$m])

3) Selection of the Wavelength of the Irradiating Laser Beam:

FIG. 6 is a graph showing the relationship between laser wavelengths ($\lambda$, [nm]) and measurable spatial wavelengths (p [µm]).

In order to determine the distance L between the photodetector and the polishing pad and the laser spot diameter $d_0$, it is necessary to select a laser wavelength. As shown in FIG. 6, as the laser wavelength $\lambda$ is shorter, the measurable limit p ($p \approx \lambda$ when $\theta = 0$ and $\beta = 90°$ in the equation (1)) of spatial wavelengths of the polishing pad topography is basically smaller.

However, as the laser wavelength is smaller, the light extinction ratio of the light intensity increases due to the scattering of light caused by the atmosphere (Rayleigh scattering intensity $y \propto \lambda^{-4}$), thus possibly causing disturbance to the scattered light from the surface to be measured.

If the light extinction ratio of the light intensity is to be set to 13.5% or smaller as indicated by the arrows in FIG. 6, then the laser wavelength used for measurement needs to be set to 450 µm (0.45 µm) or greater, and the spatial wavelength that can be measured accordingly is about 0.45 µm or greater if the angle $\theta = 0$. Similarly, if the light extinction ratio of the light intensity is to be set to 25% or smaller, than the laser wavelength used for measurement may be set to 400 nm (0.4 µm) or greater.

For example, if a small-size semiconductor laser is used then a laser beam having a wavelength greater than 450 nm, and a closest wavelength of 532 nm that is commonly used in general, can be used.

4) Wavelength Constituent Ratio:

FIG. 7 is a schematic diagram showing an intensity distribution of scattered light that is reflected and scattered by a surface of a polishing pad when the polishing pad is irradiated with a laser beam. In FIG. 7, the symbols are defined in the same manner as in FIG. 4.

The ratio of an integrated value of the intensity of scattered light in a second spatial wavelength range from a spatial wavelength $p_1$ to a spatial wavelength $p_2$ to an integrated value of the intensity of scattered light in, a first spatial wavelength range from a spatial wavelength $p_3$ to a spatial wavelength $p_4$ shown in FIG. 7 is determined by the following equation:

$$\frac{\int_{p_1}^{p_2} I(p) dp}{\int_{p_3}^{p_4} I(p) dp} [\%]$$

The above ratio is defined as a wavelength constituent ratio.

Figure 8A:
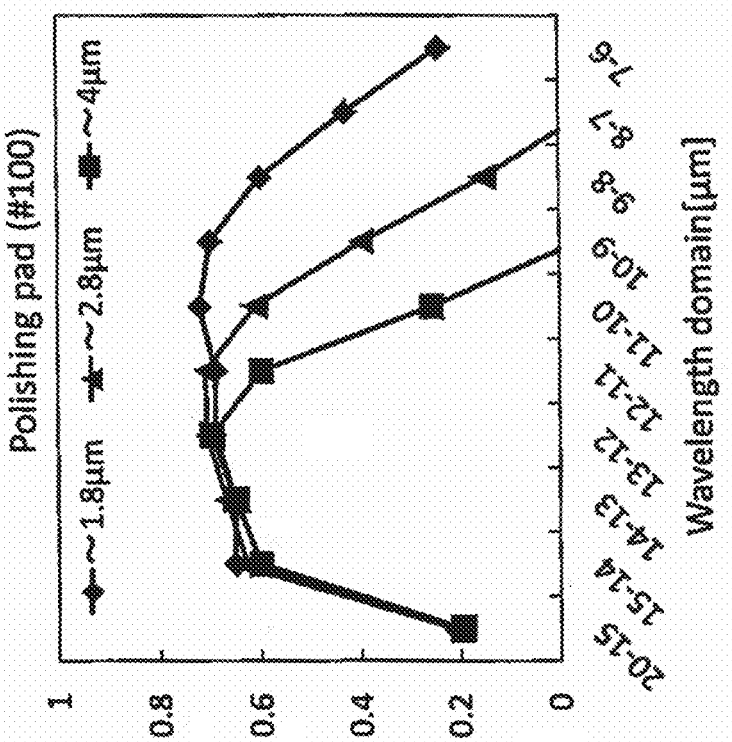
FIGS. 8A and 8B are graphs showing correlation values (vertical axis) of ratios (wavelength constituent ratios) between integrated values of light intensity in spatial wavelength (horizontal axis) ranges and integrated values (up to 30 $\mu$m) of light intensity in an overall observational area, and a polishing rate (MRR) based on the light intensity distribution obtained according to the present process.
Figure 8B:
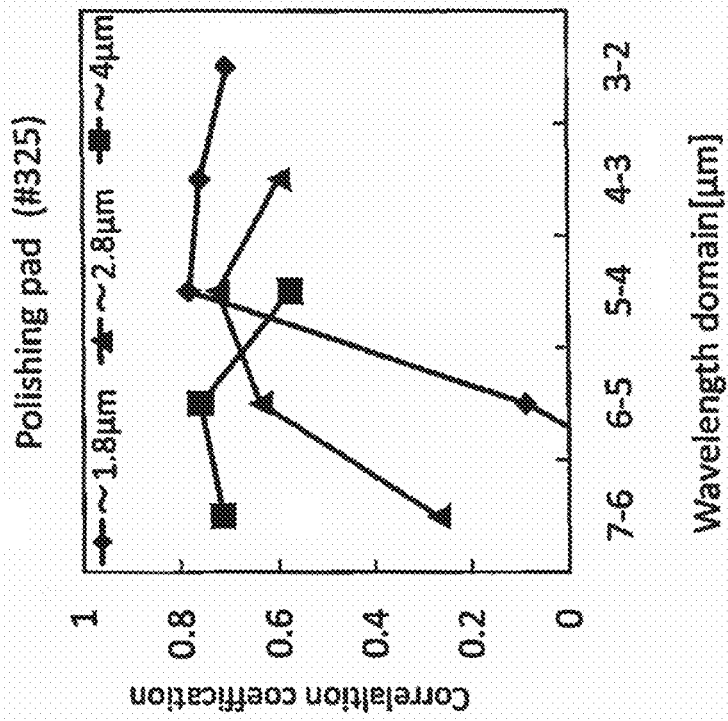

5) The Result of a Correlation Between the Wavelength Constituent Ratio and a Polishing Rate (MRR):

FIGS. 8A and 8B are graphs showing correlation values (vertical axis) of ratios (wavelength constituent ratios) between integrated values of light intensity in spatial wavelength (horizontal axis) ranges and integrated values (up to 30 µm) of light intensity in an overall observational area, and a polishing rate (MRR) based on the light intensity distribution obtained according to the present process.

FIGS. 8A and 8B illustrate characteristic of correlation values produced in an observational area having a widest measurement range from 30 to 1.8 µm, an observational area having a next widest measurement range from 30 to 2.8 µm, and an observational area having a narrowest measurement range from 30 to 4 µm, using polishing pads dressed by different dressers (#325 and #100).

As shown in FIGS. 8A and 8B, the correlation values tend to higher when the values are calculated in a wider spatial wavelength range from 30 to 1.8 µm than when the values are calculated in spatial wavelength ranges from 30 to 21 µm and from 30 to 4 µm. Therefore, it can be understood that good results are obtained by calculating integrated values of the spectrum in the wider spatial wavelength range from 30 to 1.8 µm.

Figure 9B:
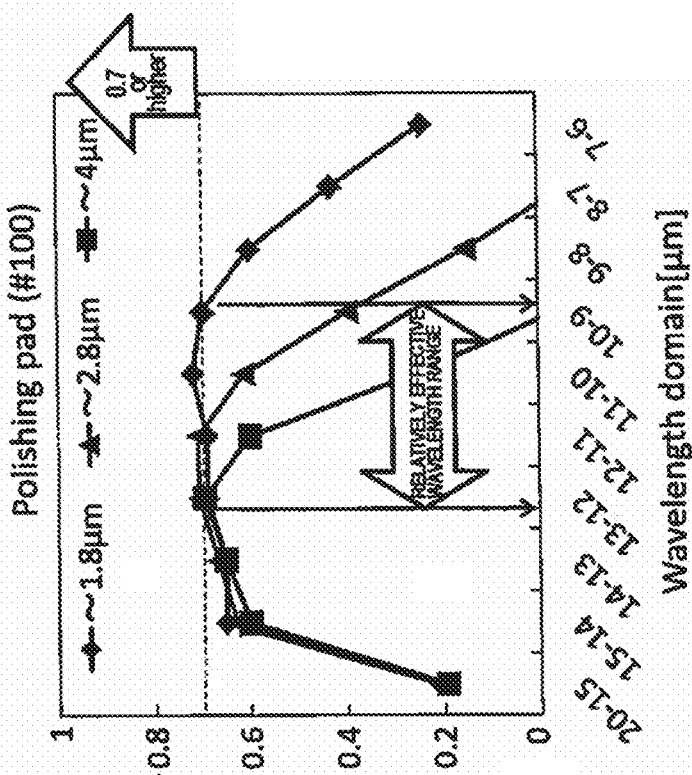
FIGS. 9A and 9B are graphs showing correlation values (vertical axis) of ratios (wavelength constituent ratios) between integrated values of light intensity in spatial wavelength (horizontal axis) ranges and integrated values (up to 30 $\mu$m) of light intensity in an overall observational area, and a polishing rate (MRR) based on the light intensity distribution obtained according to the present process.
Figure 9A:
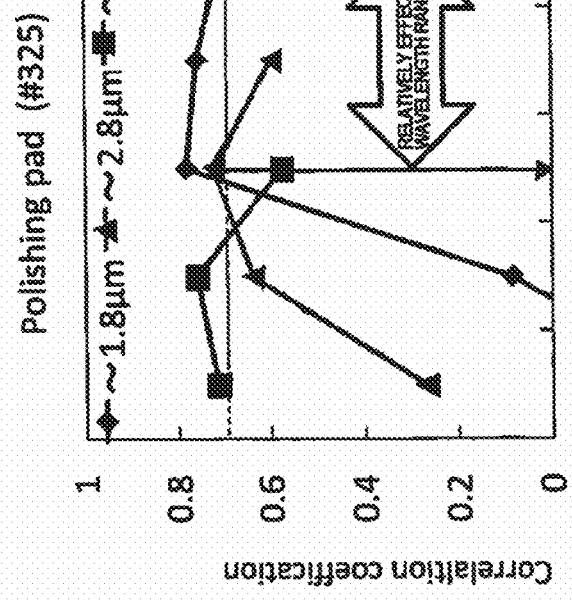

6) Identification of a Spatial Wavelength Range for Calculating a Surface Index:

FIGS. 9A and 9B are graphs showing correlation values (vertical axis) of ratios (wavelength constituent ratios) between integrated values of light intensity in spatial wavelength (horizontal axis) ranges and integrated values (up to 30 µm) of light intensity in an overall observational area, and a polishing rate (MRR) based on the light intensity distribution obtained according to the present process.

In order to grasp pad properties, a correlation coefficient value should preferably be 0.7 or greater. In the case of considering a high correlation coefficient of 0.7 or higher in FIGS. 9A and 9B, the correlation coefficient in a relatively wide wavelength range and at a smaller spatial wavelength p tends to be higher in a wider range of measurements (1.8 µm).

In the examples shown in FIGS. 9A and 9B, spatial, wavelength ranges are selected as follows:

1. The overall spatial wavelength range includes a mange from 4 to 30 µm and preferably a range from 2 to 30 µm.
2. The spatial wavelength range in the case of the polishing pad dressed with #325: 2 (1.8) to 5 µm.
3. The spatial wavelength range in the case of the polishing pad dressed with #100: 9 to 13 µm.

The correlation between the wavelength constituent ratio and the polishing rate) in the spatial wavelength range ($p_1$ to $p_2$ µm) shown in FIG. 7, as an example, was determined according to the scattered light intensity distribution obtained according to the present process. In this case, the polishing pads dressed with #100 and #325 were evaluated in the same spatial wavelength range.

Figure 10:
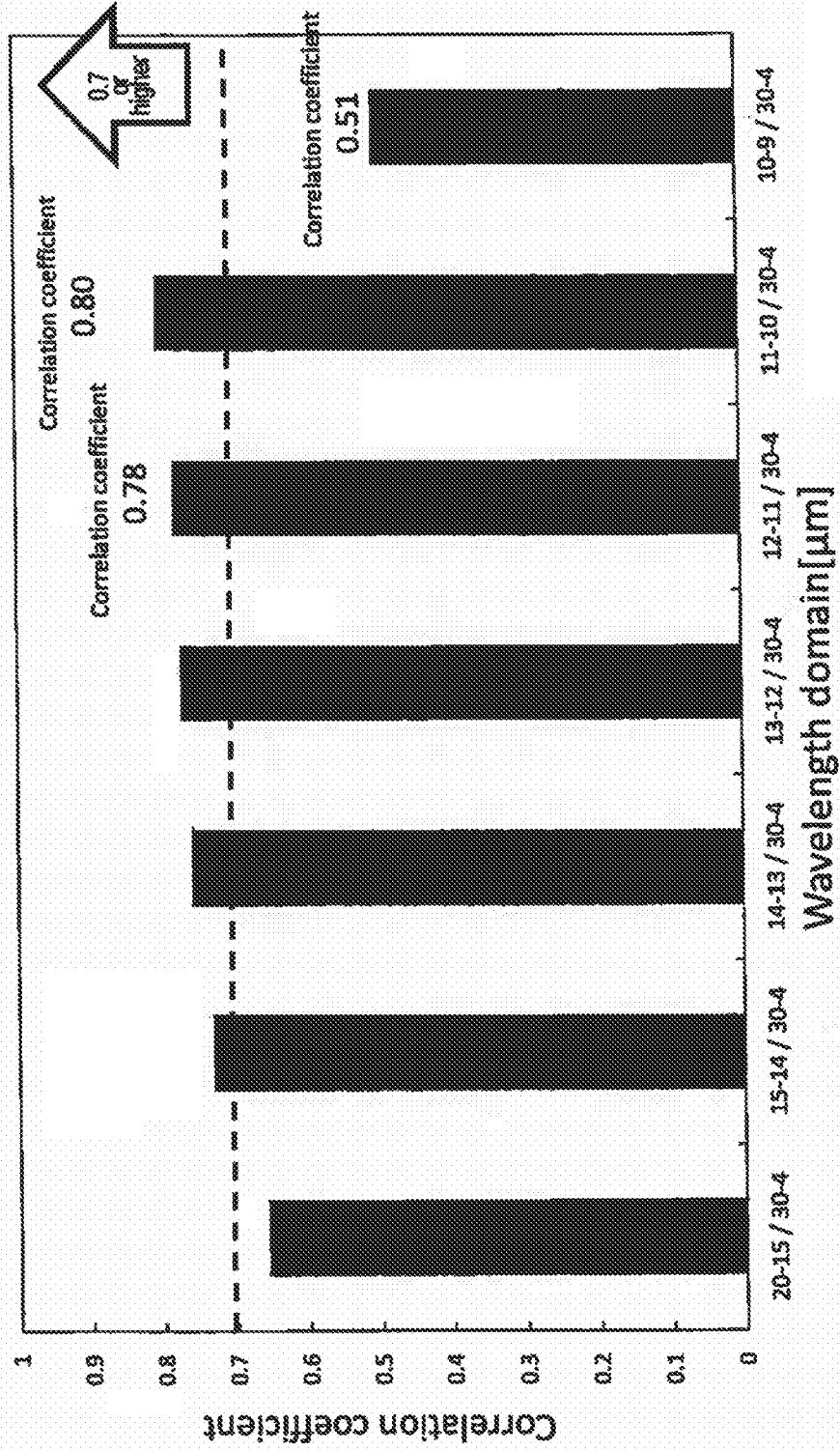
FIG. 10 is a graph showing correlation coefficient values (vertical axis) between the wavelength constituent ratios in the spatial wavelength ranges (horizontal axis) and a polishing rate (MMR)

FIG. 10 is a graph showing correlation coefficient values (vertical axis) between the wavelength constituent ratios in the spatial wavelength ranges (horizontal axis) and a polishing rate (MMR), the graph illustrating the results of the above evaluation.

It can be seen from the example shown in FIG. 10 that in the case of considering a correlation coefficient value of 0.7 or higher, which represents a high correlation coefficient, the spatial wavelength range of minute surface irregularities that contribute to polishing may be limited to a range from 10 to 15 μm.

The experimental results shown in FIGS. 8 through 10 were obtained from the apparatus configuration shown in FIGS. 1 and 2.

7) Study of Pores and Laser Beam Incident Angle θ:

As described above, it can be understood that numerical values which are highly correlated to the polishing rate (MRR) can be calculated based on the reflected light intensity spectrum corresponding to the spatial wavelengths of the pad surface topography according to the optical FFT. The polishing pad surface has minute topography caused by the dressing process, and further a configuration, pores that have originally been formed. The scattered light intensity distribution obtained according to the present process reflects the pore configuration.

The bottom portion of the pore is not brought into direct contact with the substrate that is polished. In order to grasp the polishing rate (MRR) or the situation of dressing, effects caused by the pore configuration should be eliminated as much as possible.

For eliminating the effects caused by the pore configuration as much as possible, the incident angle of the laser beam with respect to the polishing pad should be increased so that the laser beam will not reach the bottom portion of the pore. In order for the laser beam to fail to reach the bottom portion of the pore, the incident angle needs to be 45° or greater, or preferably be 80° or greater. The bottom portion of the pore that is not to be reached by the laser beam means a bottom portion of a pore having such a depth that the bottom portion will not be held in sliding contact with the substrate during polishing. Such a pore does not include a very shallow pore.

8) Study of the Reflectance and Polarization of a Laser Beam:

The laser beam is not fully reflected by the polishing pad surface, but partly enters the polishing pad. The laser beam that has entered the polishing pad is scattered and reflected by the structure (pores or the like) inside the polishing pad, and part of the light that has been scattered and reflected inside the polishing pad joins the light that is scattered and reflected by the polishing pad surface. In order to measure the surface properties of the polishing pad, it is desirable to reduce the effects caused by the laser beam which has entered the polishing pad. The reflectance of a laser beam that is reflected by a surface of a substance varies with the incident angle, and tends to be greater as the incident angle is greater. Therefore, the incident angle should preferably be selected such that the reflectance of a laser beam that is reflected by the polishing pad surface will be 50% or greater.

Further, the reflectance of a laser beam that is reflected by the polishing pad surface monotonously increases for S-polarized light as the incident angle increases, but decreases for P-polarized light as the incident angle approaches the Brewster's angle and increases as the incident angle goes beyond the Brewster's angle. Therefore, the laser beam to be applied to the polishing pad may be converted into S-polarized light by a polarizer or the like to increase reflectance on the polishing pad surface.

Figure 11:
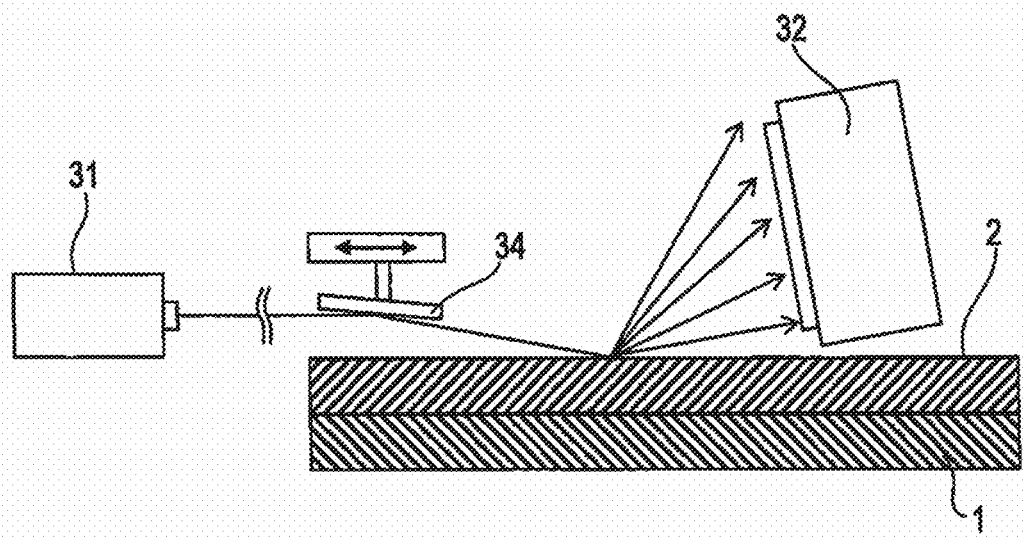
FIG. 11 is a schematic view showing an apparatus configuration for a laser beam incident angle of 80°.

FIG. 11 shows by way of example an apparatus configuration for a laser beam incident angle of 80°. As with the embodiment of FIG. 1, a laser beam emitted from a light source 31 is applied via the two mirrors 33, 34 to the polishing pad 2. The mirrors 33, 34 are set in position and angle so as to reflect the laser beam emitted from the light source 31 and to apply the laser beam at an incident angle of 80° to the polishing pad 2. Specifically, the laser beam that is emitted substantially perpendicularly from the light source 31 has its light path changed by the mirror 33 (not shown in FIG. 11) so as to travel parallel to the surface of the polishing pad 2, and then has its light path changed again by the mirror 34 so as to be applied at an incident angle of 80° to the polishing pad 2. A photodetector 32 is disposed so that specularly reflected light from the polishing pad irradiated with the laser beam is applied perpendicularly to the photodetector 32.

Since the incident angle is large, when the thickness of the polishing pad varies, the position on the polishing pad which is irradiated with the laser beam varies relatively greatly. In the configuration of FIG. 11, the mirror 34 is mounted on a horizontally moving mechanism that adjusts the mirror 34 to cause the specularly reflected light to be applied to the same position on the surface of the photodetector 32 regardless of variations in the thickness of the polishing pad 2. The apparatus may include a measuring instrument (not shown) for measuring the thickness of the polishing pad or the height of the surface of the polishing pad, and the horizontally moving mechanism may be controlled based on the measured result of the measuring instrument.

A numerical value that is strongly correlated to the CMP performance which has been obtained in the above steps is compared with a predetermined value. If the comparison result meets specific conditions, then the life or replacement timing of the polishing pad or the dresser, or an abnormality of the pad surface properties or the dressing state is displayed on a display unit of the processing device 36.

The processing device 36 also has a function to convert the numerical value, that is strongly correlated to the CMP performance, which has been obtained in the above steps into a CMP parameter, particularly dressing conditions (surface pressure, rotational speed, and swinging pattern) in the light of predetermined conditions. For example, such a function may be a function to obtain, in advance, a formula representing the correlation between the above numerical value, the dressing conditions, and the CMP performance, substitute the above numerical value measured after the dressing process into the formula to calculate dressing conditions for making the CMP performance constant at all tunes, and apply the calculated dressing conditions to a next dressing process.

FIGS. 12A and 12B are flowcharts of sequences for changing dressing conditions using numerical values obtained by the process shown in FIGS. 4 through 10 and sequences for displaying an alarm.

In the example shown in FIG. 12A, after polishing a substrate, the polishing pad 2 is dressed, and then the polishing pad surface is measured. Then, a pad surface index is calculated, and it is judged whether the pad surface index falls within a predetermined range or not lithe pad surface index does not fall within the predetermined range (in the ease of NO), then the next dressing conditions are changed. If the pad surface index falls within the predetermined range (in the case of YES), then the dressing conditions are not changed, and the next dressing process is carried out under the same dressing conditions:

An example of changed dressing conditions is shown in Table 1,

TABLE 1

| Dressing parameters | Pad surface index is smaller than predetermined range | Pad surface index is greater than predetermined range |
|---|---|---|
| Dressing load | Increase | Decrease |

TABLE 1-continued

| | | |
|---|---|---|
| Dressing rotational speed | Increase | Decrease |
| Dressing time | Increase | Decrease |

In the example shown in FIG. 12B, after polishing a substrate, the polishing pad 2 is dressed, and then the polishing pad surface is measured. Then, a pad surface index is calculated, and it is judged whether the pad surface index falls within a normal range or not. If the pad surface index does not fall within the normal range (in the case of NO), then any one of alarms regarding a dresser life, a polishing pad life, and a polishing pad surface abnormality is displayed. In this case, an arithmetic equation of a pad surface index representing a dresser life, a polishing pad life, and a polishing pad surface abnormality, and normal range for a pad surface index have been determined in advance. If the pad surface index falls within the normal range (in the case of YES), then the process is continued.

An example of sequences for polishing a substrate, dressing a polishing pad and monitoring a surface of the polishing pad, using the polishing apparatus shown in FIGS. 1 and 2, will be described below with reference to FIG. 13.

As shown in FIG. 13, a substrate starts to be processed, and the substrate is polished, Specifically, the polishing liquid (slurry) is supplied from the polishing liquid supply nozzle 3 onto the polishing pad 2. While the carrier 10 is being rotated, the carrier 10 is lowered to press the substrate W against the rotating polishing pad 2 under a predetermined polishing pressure, thereby starting a polishing process for polishing a metal film or an insulating film on the substrate. An in-situ dressing process in which dressing is performed simultaneously with the polishing process may be carried out.

After supply of the polishing liquid from the polishing liquid supply nozzle 3 is stopped, the polishing pad 2 is supplied with pure water to perform water polishing of the substrate, thereby cleaning the substrate on the polishing pad 2. Thereafter, the polished substrate is delivered outside of the polishing pad 2 by the carrier 10, and transferred to a transfer device such as a pusher.

Then, the polishing pad 2 is dressed. Specifically, the polishing pad 2 is rotated and the dresser 22 is rotated. Then, the dresser arm 21 is lowered to press the dressing member 22a on the lower surface of the dresser 22 against the rotating polishing pad 2. In such state, the dresser arm 21 is swung. While the polishing pad 2 is being dressed, the polishing liquid supply nozzle 3 (see FIG. 1) supplies pure water as a dressing liquid to the polishing pad 2.

Then, the polishing pad surface property measuring device 30 monitors the surface of the polishing pad 2. In the monitoring process, a pad surface index is calculated as described above with reference to FIGS. 4 through 10, and the prescribed judgement such as a change of the dressing conditions or a display of an alarm of a polishing pad life or a polishing pad surface abnormality as described above with reference to FIGS. 12A and 12B is performed.

After the monitoring process is finished, the substrate processing sequence is completed. The monitoring process may be carried out during the polishing process or the dressing process.

While the embodiment of the present invention has been described above, the present invention is not limited to the above embodiment, but may be reduced to practice in various different forms within the scope of the technical concept thereof.

What is claimed is:

1. A polishing apparatus for polishing a substrate, comprising:
   a polishing table configured to hold a polishing pad and rotate the polishing pad; and
   a measuring device arranged above the polishing table for measuring a surface of the polishing pad, the measuring device comprising:
      a laser beam source configured to emit a laser beam;
      a first mirror having a reflecting surface and configured to reflect the laser beam emitted from the laser beam source;
      a second mirror having a reflecting surface and configured to reflect the laser beam reflected by the first mirror and to apply reflected laser beam to a top surface of the polishing pad; and
      a photodetector configured to detect scattered light that is reflected and scattered by the polishing pad held by the polishing table;
      wherein said reflecting surface of said second mirror is inclined with respect to the top surface of the polishing pad to apply said laser beam to the top surface of the polishing pad at an incident angle of 45° or greater so that the laser beam does not reach a bottom portion of a pore formed in the surface of the polishing pad.

2. A polishing apparatus for polishing a substrate, comprising:
   a polishing table configured to hold a polishing pad and rotate the polishing pad; and
   a measuring device arranged above the polishing table for measuring a surface of the polishing pad, the measuring device comprising:
      a laser beam source configured to emit a laser beam;
      a first mirror having a reflecting surface and configured to reflect the laser beam emitted from the laser beam source;
      a second mirror having a reflecting surface and configured to reflect the laser beam reflected by the first mirror and to apply reflected laser beam to a top surface of the polishing pad; and
      a photodetector configured to detect scattered light that is reflected and scattered by the polishing pad held by the polishing table;
      wherein said reflecting surface of said second mirror is inclined with respect to the top surface of the polishing pad to apply said laser beam to the top surface of the polishing pad at such an incident angle that the reflectance of the light from the surface of the polishing pad is 50% or greater.

3. The polishing apparatus according to claim 1, further comprising:
   a carrier configured to hold a substrate as an object to be polished and to press the substrate against the polishing pad; and
   a dresser configured to dress the polishing pad.

4. The polishing apparatus according to claim 2, further comprising:
   a carrier configured to hold a substrate as an object to be polished and to press the substrate against the polishing pad; and
   a dresser configured to dress the polishing pad.

5. The polishing apparatus according to claim 1, wherein said reflecting surface of said second mirror is inclined with respect to the top surface of the polishing pad to apply said laser beam to the top surface of the polishing pad at the incident angle of 80° or greater.

6. The polishing apparatus according to claim 3, further comprising:
an arm configured to move said carrier, said laser beam source being fixed to said arm.

7. The polishing apparatus according to claim 4, further comprising:
an arm configured to move said carrier, said laser beam source being fixed to said arm.

8. The polishing apparatus according to claim 1, wherein said measuring device further comprises a horizontally moving mechanism configured to move said second mirror in a horizontal direction along the top surface of the polishing pad.

9. The polishing apparatus according to claim 2, wherein said measuring device further comprises a horizontally moving mechanism configured to move said second mirror in a horizontal direction along the top surface of the polishing pad.

10. The polishing apparatus according to claim 1, wherein said photodetector performs an optical Fourier transform on the detected scattered light to produce an intensity distribution corresponding to a spatial wavelength spectrum based on surface topography of the polishing pad.

11. The polishing apparatus according to claim 2, wherein said photodetector performs an optical Fourier transform on the detected scattered light to produce an intensity distribution corresponding to a spatial wavelength spectrum based on surface topography of the polishing pad.

12. A polishing apparatus for polishing a substrate, comprising:
a polishing pad having at least a pore formed in a surface thereof; and
a measuring device arranged above the polishing pad for measuring a surface of the polishing pad, the measuring device comprising:
a laser beam source configured to emit a laser beam;
a first mirror having a reflecting surface and configured to reflect the laser beam emitted from the laser beam source;
a second mirror having a reflecting surface and configured to reflect the laser beam reflected by the first mirror and to apply reflected laser beam to a top surface of the polishing pad; and
a photodetector configured to detect scattered light that is reflected and scattered by the polishing pad held by the polishing table,
wherein said reflecting surface of said second mirror is inclined with respect to the top surface of the polishing pad to apply said laser beam to the top surface of the polishing pad at such an incident angle that the laser beam does not reach a bottom portion of the at least a pore formed in the surface of the polishing pad.

* * * * *